United States Patent
Kaneko et al.

(10) Patent No.: US 11,666,899 B2
(45) Date of Patent: Jun. 6, 2023

(54) SAFETY CABINET

(71) Applicant: Hitachi Industrial Equipment Systems Co., Ltd., Tokyo (JP)

(72) Inventors: Takeshi Kaneko, Tainai (JP); Takahiro Kashima, Tokyo (JP)

(73) Assignee: Hitachi Industrial Equipment Systems Co., Ltd., Tokyo (JP)

( * ) Notice: Subject to any disclaimer, the term of this patent is extended or adjusted under 35 U.S.C. 154(b) by 413 days.

(21) Appl. No.: 16/759,198

(22) PCT Filed: Jan. 23, 2019

(86) PCT No.: PCT/JP2019/002048
§ 371 (c)(1),
(2) Date: Apr. 24, 2020

(87) PCT Pub. No.: WO2019/207866
PCT Pub. Date: Oct. 31, 2019

(65) Prior Publication Data
US 2020/0316581 A1 Oct. 8, 2020

(30) Foreign Application Priority Data
Apr. 24, 2018 (JP) .............................. JP2018-083426

(51) Int. Cl.
*B01L 1/02* (2006.01)
*F24F 11/89* (2018.01)
(Continued)

(52) U.S. Cl.
CPC .............. *B01L 1/025* (2013.01); *F24F 7/007* (2013.01); *F24F 7/06* (2013.01); *F24F 11/30* (2018.01);
(Continued)

(58) Field of Classification Search
CPC ....... B01L 1/025; B01L 2200/06; F24F 11/89; F24F 11/30; F24F 7/007; F24F 7/06; C12M 1/12
See application file for complete search history.

(56) References Cited

U.S. PATENT DOCUMENTS 5,792,435 A * 8/1998 Mueller .................... A61L 2/24
422/302
7,090,709 B2 * 8/2006 Ono ...................... B08B 15/023
55/385.2
(Continued)

FOREIGN PATENT DOCUMENTS

BR 202013027639 U2 11/2015
CN 101224437 A 7/2008
(Continued)

OTHER PUBLICATIONS

Huang, CN101569867A English machine translation, Nov. 4, 2009 (Year: 2009).*
(Continued)

*Primary Examiner* — Avinash A Savani
*Assistant Examiner* — Dana K Tighe
(74) *Attorney, Agent, or Firm* — Crowell & Moring LLP

(57) ABSTRACT

A safety cabinet includes an operation stage on which an operation is performed, an operation space in which an operator performs the operation, a front panel disposed in front of the operation space, an operation opening connected to the operation space, exhausting means that suctions air from the operation opening and exhausts air in the operation space outside the safety cabinet through air purifying means, and visualizing means that visualizes an air flow in the operation space.

3 Claims, 8 Drawing Sheets

(51) Int. Cl.
    *F24F 11/30*     (2018.01)
    *F24F 7/007*     (2006.01)
    *F24F 7/06*     (2006.01)
    *C12M 1/12*     (2006.01)

(52) U.S. Cl.
    CPC ........... *F24F 11/89* (2018.01); *B01L 2200/06* (2013.01); *C12M 1/12* (2013.01)

(56) References Cited

U.S. PATENT DOCUMENTS

| | | |
|---|---|---|
| 2008/0150404 A1 | 6/2008 | Ono |
| 2017/0120233 A1 | 5/2017 | Rindoks et al. |
| 2018/0001315 A1 | 1/2018 | Kaneko et al. |

FOREIGN PATENT DOCUMENTS

| | | | |
|---|---|---|---|
| CN | 101362107 A | | 2/2009 |
| CN | 101569867 A | * | 11/2009 |
| CN | 201514313 U | | 6/2010 |
| CN | 202136987 U | | 2/2012 |
| CN | 202762328 U | | 3/2013 |
| CN | 203535841 U | | 4/2014 |
| CN | 205020096 U | | 2/2016 |
| CN | 106622404 A | | 5/2017 |
| CN | 106803366 A | | 6/2017 |
| EP | 2 014 365 A2 | | 1/2009 |
| JP | 62-67419 A | | 3/1987 |
| JP | 8-136568 A | | 5/1996 |
| JP | 2002-22597 A | | 1/2002 |
| JP | 2002-143696 A | | 5/2002 |
| JP | 2008-295448 A | | 12/2008 |
| JP | 2015-224819 A | | 12/2015 |
| JP | 2016-165249 A | | 9/2016 |
| JP | 2017-78527 A | | 4/2017 |
| JP | 2017-146086 A | | 8/2017 |

OTHER PUBLICATIONS

Hashimoto, JPS62067419A English machine translation, Mar. 27, 1987 (Year: 1987).*

Kawabata, JP2002022597A English machine translation, Jan. 23, 2002 (Year: 2002).*

Xu, CN203535841U English machine translation, Apr. 9, 2014 (Year: 2014).*

Chinese-language Office Action issued in Chinese Application No. 201980005504.3 dated May 6, 2021 with English translation (17 pages).

International Search Report (PCT/ISA/210) issued in PCT Application No. PCT/JP2019/002048 dated Apr. 9, 2019 with English translation (five (5) pages).

Japanese-language Written Opinion (PCT/ISA/237) issued in PCT Application No. PCT/JP2019/002048 dated Apr. 9, 2019 (five (5) pages).

* cited by examiner

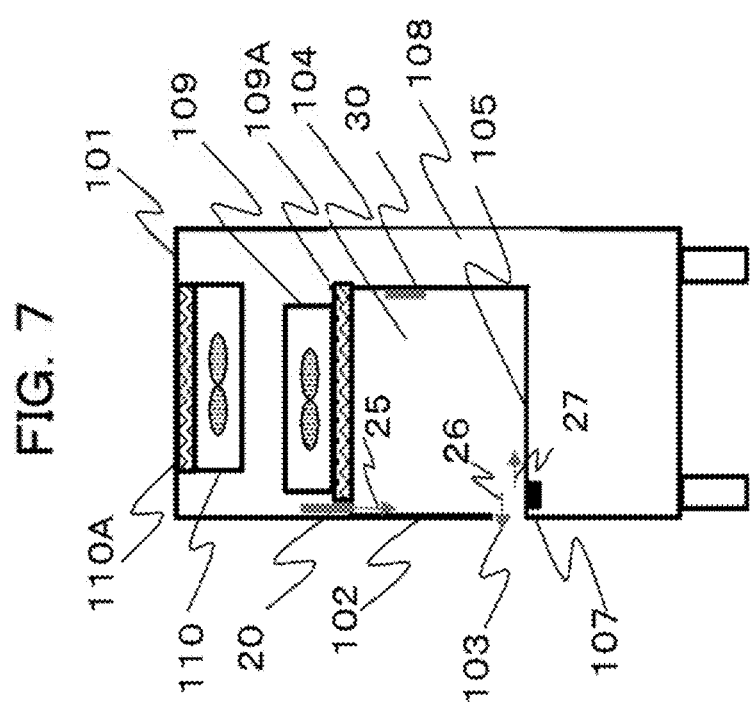

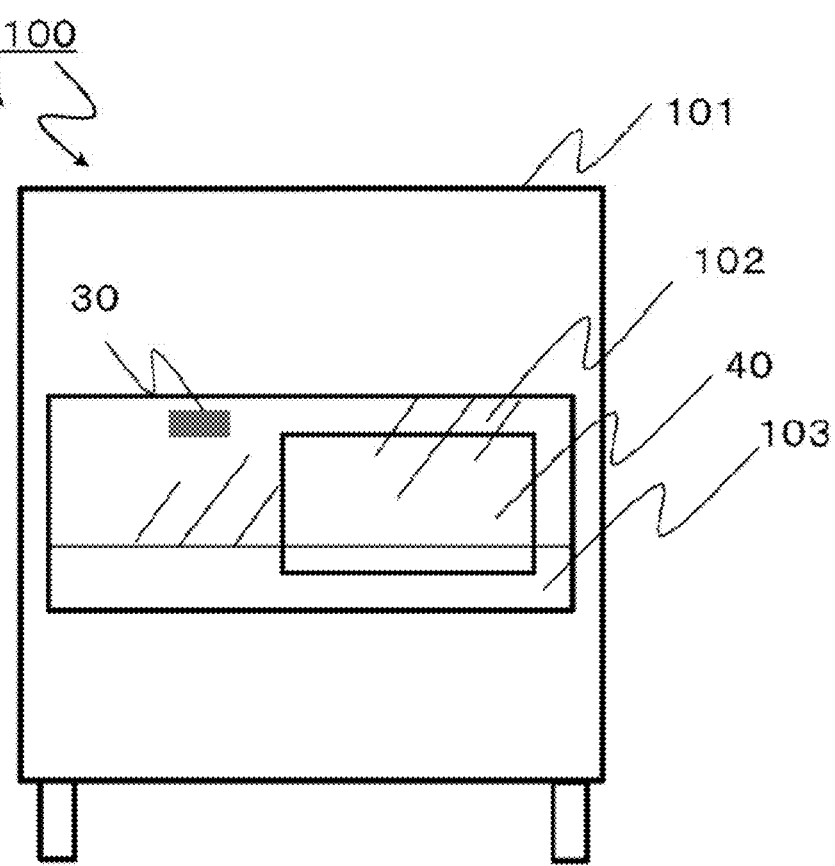
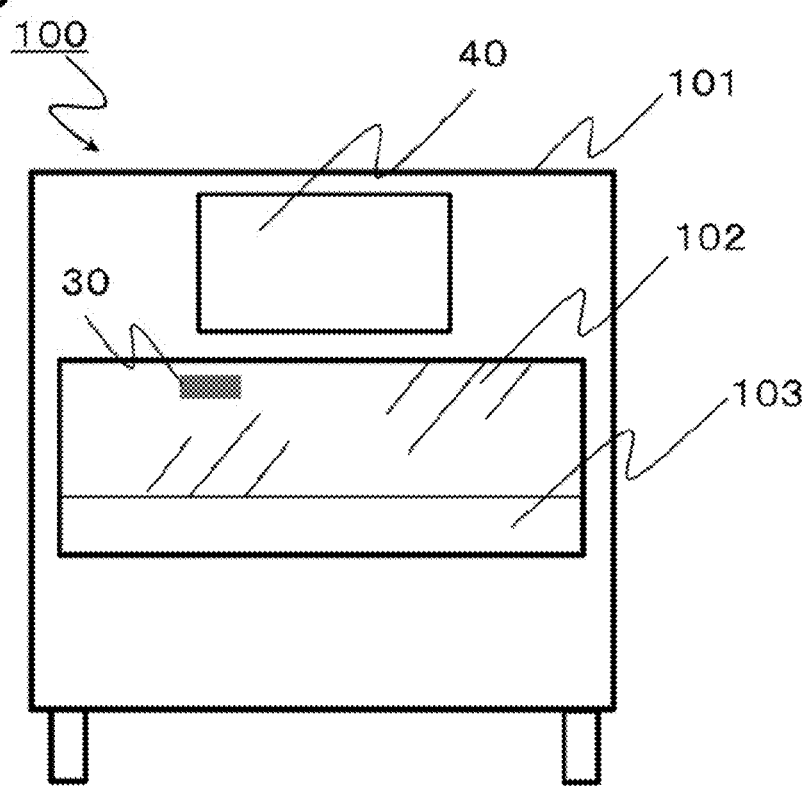

SAFETY CABINET

TECHNICAL FIELD

The present invention relates to a safety cabinet which is equipment that realizes a safe operating environment in handling microorganisms, pathogens, or the like.

BACKGROUND ART

In the related art, when microorganisms, pathogens, or the like are handled, a safety cabinet is used to maintain an internal purity, to physically isolate the microorganisms and the pathogens to be handled from the human and the environment, and thus to allow an operation to be safely performed.

As the safety cabinet, there are known techniques disclosed in Patent Documents 1 and 2.

Patent Document 1 discloses a safety cabinet that exhausts air outdoors through an open duct connection and issues an alarm when there is a possibility that a defect occurs with an outdoor exhaust duct system to cause the exhaust air of the safety cabinet, which contains a small amount of volatile noxious substances, to leak from an opening portion of an open duct to a laboratory.

Patent Document 2 discloses a technique where when an operator performs an operation using a safety cabinet while confirming a standard operation procedure document or specimen data, a display device such as a monitor screen provided in the safety cabinet is disposed at a position where the display device is not affected by the diffused reflection of light from a fluorescent lamp or a deterioration due to irradiation from a sterilization lamp, does not become resistance to an airflow path, and is also protected from a decontamination operation, and a contamination is prevented from adhering to a portion related to display.

CITATION LIST

Patent Document

Patent Document 1: JP 2017-78527 A
Patent Document 2: JP 2016-165249 A

SUMMARY OF THE INVENTION

Problems to be Solved by the Invention

When the safety cabinet is used, the operator inserts the hands from an opening portion to perform an operation and thus a turbulence occurs in inside air. It is desirable that the operator learns a motion and an operation procedure which minimizes the turbulence.

Patent Document 1 and Patent Document 2 do not disclose any method for allowing the operator to understand how the operation of the operator affects a turbulence of an air flow.

In the safety cabinet of the related art, it is difficult for the operator to understand that an air flow flowing in from outside or an air flow to cause air in an operation space to flow out occurs due to a motion or the like of the operator to deteriorate the purity of the operation space.

An object of the present invention is to provide a safety cabinet that allows an operator to understand an air flow during an operation.

Solutions to Problems

According to one exemplary aspect of the present invention, there is provided a safety cabinet including: an operation stage on which an operation is performed; an operation space in which an operator performs the operation; a front panel disposed in front of the operation space; an operation opening connected to the operation space; exhausting means that suctions air from the operation opening and exhausts air in the operation space outside the safety cabinet through air purifying means; and visualizing means that visualizes an air flow in the operation space.

Effects of the Invention

According to the present invention, the operator can understand the air flow during the operation.

BRIEF DESCRIPTION OF THE DRAWINGS

FIG. 7 is a schematic side view of the safety cabinet illustrating a plurality of mist flows in an operation space.

FIGS. 8A and 8B are schematic front views of a safety cabinet for describing a third embodiment.

MODE FOR CARRYING OUT THE INVENTION

Hereinafter, embodiments will be described with reference to FIGS. 1 to 8.

First Embodiment

Figure 1:
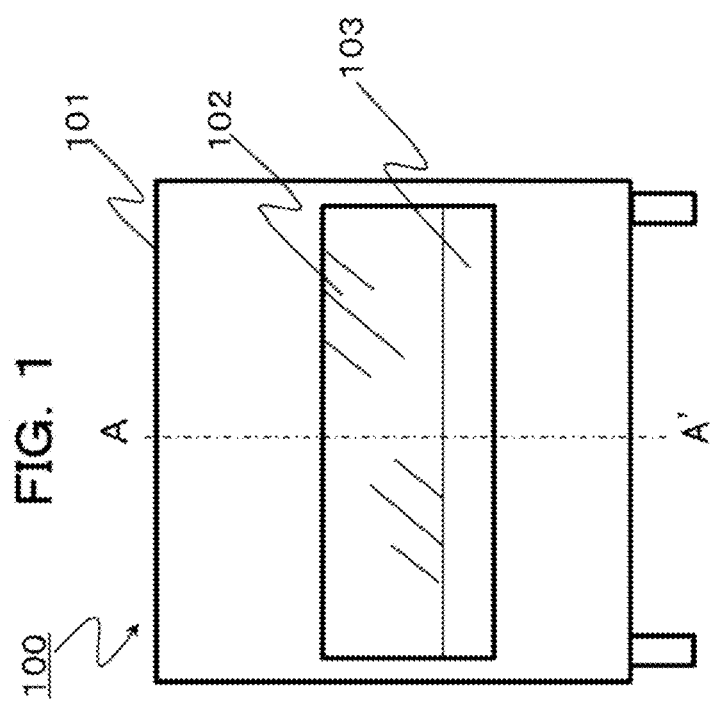
FIG. 1 is a schematic front view of a safety cabinet in a first embodiment.
Figure 2:
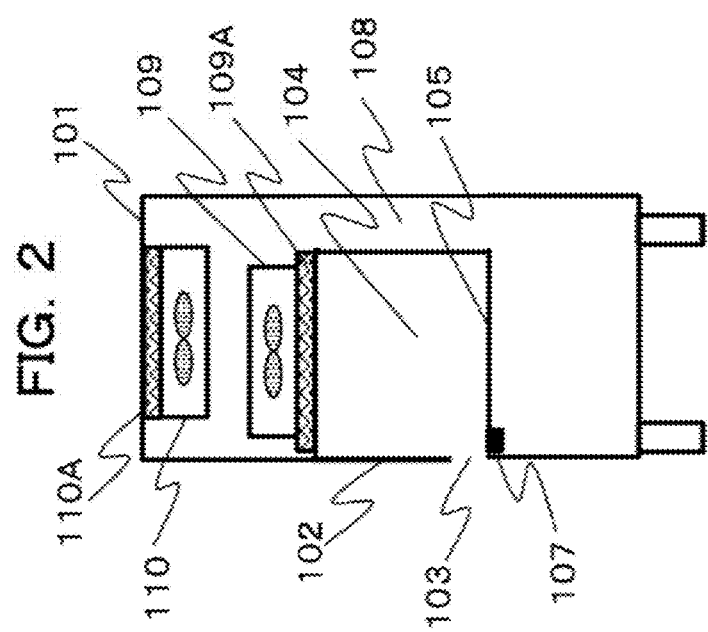
FIG. 2 is a schematic side view of the safety cabinet when a cross section A-A' in FIG. 1 is seen from right.

FIG. 1 illustrates a schematic front view of a safety cabinet. In addition, FIG. 2 illustrates a schematic side view of the safety cabinet when a cross section A-A' in FIG. 1 is seen from right.

An opening is provided in a central region of a housing 101 of a safety cabinet 100, and an operation space 104 is provided at the rear of the opening. A front panel 102 is provided on a front surface side of the operation space 104 so as to block an upper portion of the opening, and an operation opening 103 is provided below the front panel 102. An operator inserts the hands into the operation space 104 from the operation opening 103 to perform an operation. The front panel 102 is made of a transparent material such as a glass, and the operator can see an operation through the front panel.

An operation stage 105 which is substantially flat is provided in a bottom surface of the operation space 104, and the operator performs an operation on the operation stage. An intake port 107 leading downward is provided on a front side of the operation stage 105 in the vicinity of the operation opening 103. The intake port 107 is formed as, for example, a slit that extends along the operation opening 103 in a rightward and leftward direction of the housing 101. A back flow path 108 leading from the intake port 107 to an upper portion of the housing 101 is provided on a back surface side of the operation space 104.

A blowout side fan filter unit (FFU) 109 is provided above the operation space 104. The blowout side FFU 109 includes a fan that is air blowing means driven to rotate by a motor, and a filter that removes microparticles, for example, a HEPA filter 109A that is air purifying means. Purified air from which the microparticles have been removed is blown out into the operation space 104 by the blowout side FFU 109. An exhaust side fan filter unit (FFU) 110 is provided in the upper portion of the housing 101 to remove microparticles from a part of air and exhaust the part of air outside the device through a filter, for example, a HEPA filter 110A.

Figure 3:
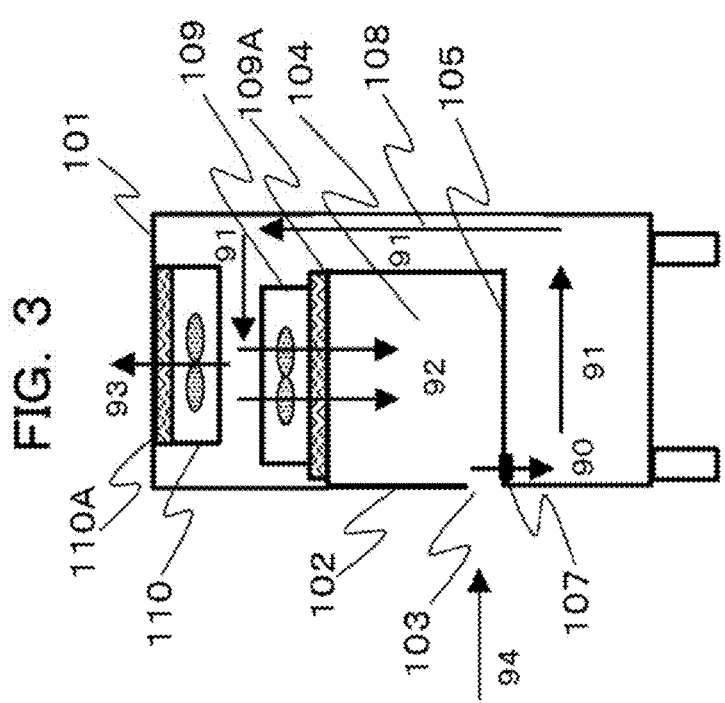
FIG. 3 is a schematic side view of the safety cabinet in which an air flow is indicated by arrows.

In FIG. 3, an air flow during operation of the safety cabinet is indicated by arrows. An air 90 which is suctioned from the intake port 107 on a front surface side of the operation stage 105 is blown, as denoted by reference sign 91, into the operation space 104 from the blowout side FFU 109 through a lower portion of the housing 101, the back flow path 108, and the upper portion of the housing 101. Since purified air from which the microparticles have been removed by the HEPA filter 109A of the blowout side FFU 109 is blown into the operation space 104, the operation space 104 is maintained in a purified state.

In this case, when there is only an air flow, which is denoted by reference sign 92, into the operation space 104, air in the operation space 104 leaks outside, which is a concern. For this reason, the exhaust side FFU 110 is provided to discharge a part of air outside through the HEPA filter 110A. Accordingly, the pressure in the operation space 104 decreases, and an air flow 94 which is to be introduced from outside to inside through the operation opening 103 below the front panel 102 is generated. When the air flow 94 flows into the operation space 104 as it is, the purity of the operation space deteriorates.

However, the air volume of the air flow 92 which is blown out into the operation space 104 from the blowout side FFU 109 and the air volume of an air flow 93 which is exhausted outside from the exhaust side FFU 110 are properly controlled, so that all of the air 94 flowing in from the operation opening 103 and the majority of the air 92 blown into the operation space 104 are suctioned from the intake port 107. Therefore, an atmospheric barrier (air barrier) which prevents the air 94 from flowing into the operation space 104 from the operation opening 103 is formed by the air flow 92 which is blown out into the operation space 104.

Accordingly, it is possible to realize an equilibrium state where the air from outside does not contaminate the operation space 104 and non-purified inside air does not leak outside. In addition, accordingly, even when the operator inserts the hands into the operation space 104 through the operation opening 103 to perform an operation, it is possible to realize the maintenance of the purity and the prevention of contamination.

Figure 4:
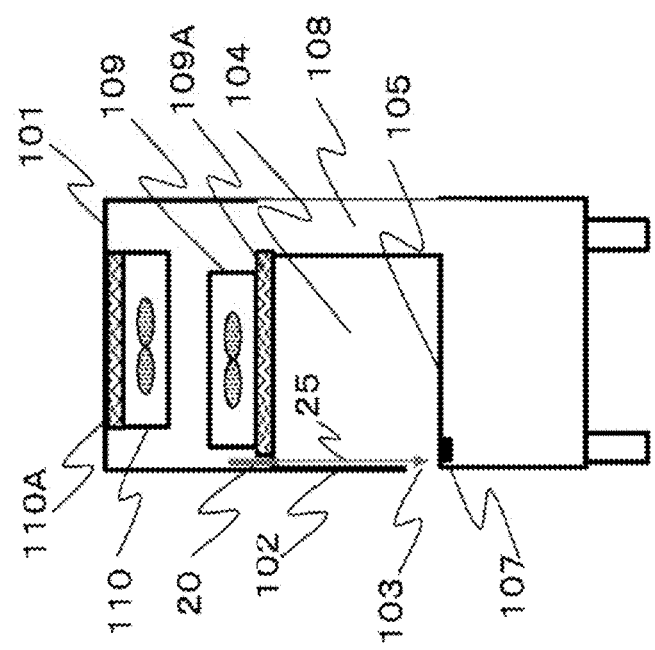
FIG. 4 is a schematic side view of the safety cabinet for describing the first embodiment.

FIG. 4 is a schematic side view of the safety cabinet 100 for describing the first embodiment. In the first embodiment, a mist generating nozzle 20 is provided inside the front panel and on a front panel 102 side of an upper portion of the operation space 104. The mist generating nozzle 20 generates a mist such that a mist flow can be visualized.

Accordingly, as illustrated in FIG. 3, the mist descends together with a downflow which is the air flow 92 in the operation space 104. As denoted by reference sign 25, the mist flows downward along an inner side of the front panel 102.

In a high-purity state, the mist becomes a linear flow that is suctioned into the intake port 107 as it is. It is preferable that the type of the mist is obtained by micronizing water using ultrasonic waves. The mist is a mist obtained by a so-called ultrasonic humidifier. In addition, a gas generated from dry ice may be introduced through a pipe.

In addition, in many cases, a variety of gases are used in a facility where the safety cabinet 100 is used. Among the gases, particularly, a gas generated from a liquefied nitrogen cylinder may be introduced through a pipe and the gas may be used as a mist gas. In any case, the occurrence of contamination due to the mist is to mistake the means for the ends, and thus the mist is required to not lead to the generation of microparticles.

The visualization of an air flow using a mist may be performed not during an actual operation but during a training session or during the examination of an operation procedure. A user such as an operator determines whether to generate or stop a mist by selecting a mist generation mode using a generation switch or touch panel that is provided as means which receives an instruction for the mist generation mode in the housing 101. In order to prevent the user from forgetting cancelling the mist generation mode, a timer mechanism may be provided such that the generation of a mist is stopped in a certain time.

According to the first embodiment, since the operator can visually observe the air flow in the operation space 104 to be able to notice an air turbulence caused by his or her own operation, the operator can learn a motion and an operation procedure which minimizes the turbulence.

Second Embodiment

Figure 5:
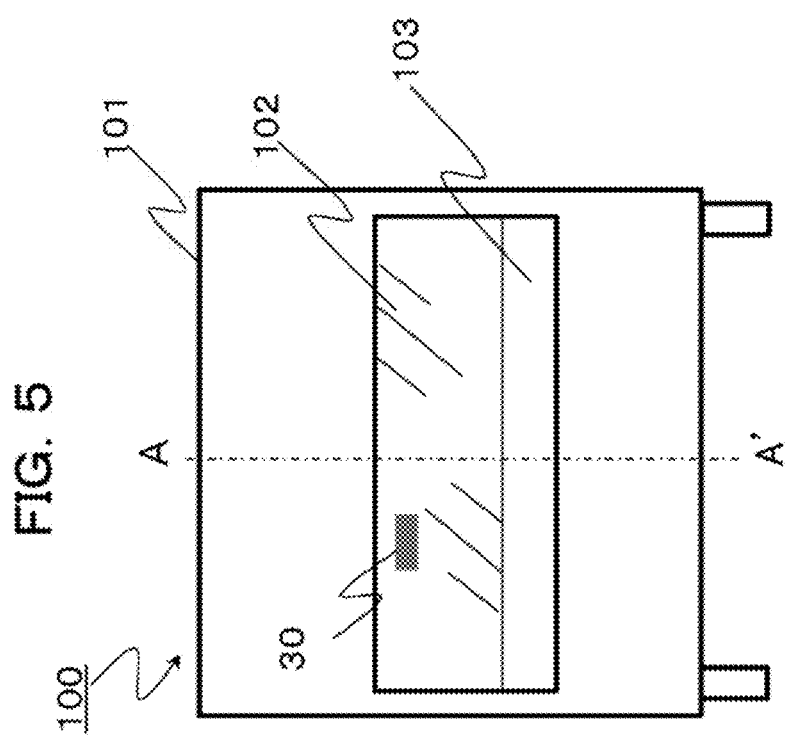
FIG. 5 is a schematic front view of a safety cabinet for describing a second embodiment.
Figure 6:
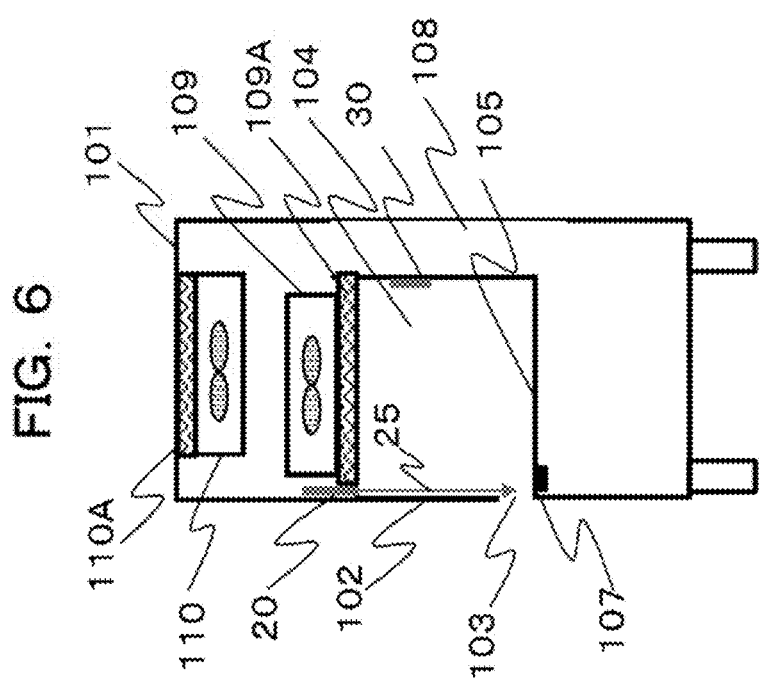
FIG. 6 is a schematic side view of the safety cabinet for describing the second embodiment.

FIG. 5 is a schematic front view of a safety cabinet for describing a second embodiment. FIG. 6 is a schematic side view of the safety cabinet when the cross section A-A' in FIG. 5 is seen from right. Descriptions duplicated in the first embodiment will be omitted. In the second embodiment, not only visual confirmation is performed by an operator, but also an image including a mist flow is acquired by a camera 30 as imaging means; and thereby, whether or not an operation of the operator is proper can be determined from the direction of the mist flow. A propriety determination process is provided as a training mode, so that the operator can understand the propriety of an operation substantially in real time while performing the operation.

As a criteria for determining the propriety, air flows in the operation space 104 illustrated in FIG. 7 can be used. FIG. 7 is a schematic side view of the safety cabinet particularly illustrating a plurality of mist flows in the operation space 104. For example, in a case where an image of an operating state and mist flows is acquired by one or a plurality of cameras and the occurrence of a mist flow 26 from the operation space 104 toward the operation opening 103 and a mist flow 27 from the operation opening 103 toward the operation space 104 as illustrated in FIG. 7 is detected, a control unit (not illustrated) can automatically determine the propriety of the operating state as a case where an operation of the operator or a behavior of the operator is improper.

The propriety of the operating state can be displayed in the form of pass or fail, a score, or the like, and may be displayed by voice, a lamp, a touch panel, or a display. The operating state and the propriety or the score of the operating state are collectively stored in an external storage device using a network connected to the safety cabinet 100, so that information on motions and operations more proper in the related field can be accumulated, which can lead to realizing an operation that is not dependent on the operator and has a small variation.

Third Embodiment

FIG. 8 is a schematic front view of a safety cabinet for describing a third embodiment. The third embodiment is a safety cabinet including a display 40 as a display unit. Descriptions duplicated in the first embodiment will be omitted. The display 40 may be disposed at a position where an operator can see the display 40 while performing an operation. For example, as illustrated in FIG. 8(*a*), the display 40 may be disposed in the back flow path 108 at the rear of the operation space 104 or outside the back flow path 108, and the operator may see the display 40 through the front panel 102 that is transparent. In addition, as illustrated in FIG. 8(*b*), the display 40 may be disposed in an upper portion of the front panel 102 in a front surface of the housing 101.

In addition, a mode called the training mode is set and the control unit causes the display 40 to display an overlay of his or her own motion on an exemplary motion display, so that the operator can more visually understand which motion is improper. In addition, the propriety of the operation or the like is machine learnt based on an image of the operating state and the mist flow using an external artificial intelligence connected to the safety cabinet 100, and the operator is notified of a result of learning about an operation or behavior which is optimal in a tissue culture operation, so that the operator can understand the optimal operation or the like.

REFERENCE SIGNS LIST

20 Mist generating nozzle
30 Camera
40 Display
100 Safety cabinet
101 Housing
102 Front panel
103 Operation opening
104 Operation space
105 Operation stage
107 Intake port
108 Back flow path
109 Blowout side fan filter unit (FFU)
109A Blowout side HEPA filter
110 Exhaust side fan filter unit (FFU)
110A Exhaust side HEPA filter

The invention claimed is:

1. A safety cabinet comprising:
an operation stage on which an operation is performed;
an operation space in which an operator performs the operation;
a front panel disposed in front of the operation space;
an operation opening connected to the operation space;
exhausting means that suctions air from the operation opening and exhausts air in the operation space outside the safety cabinet through air purifying means;
visualizing means that visualizes an air flow in the operation space, wherein
the visualizing means includes means that generates a mist, and
a touch panel that generates or stops the mist based on an input by the operator; and
an imaging unit that acquires an image of a mist flow, wherein the safety cabinet is configured to determine a state of the operation performed by the operator, based on the image acquired by the imaging unit.

2. The safety cabinet according to claim 1, further comprising
a display unit,
wherein the safety cabinet is also configured to cause the display unit to display an overlay of a motion of the operator on an exemplary motion display.

3. The safety cabinet according to claim 1,
wherein the mist is generated downward from an upper portion on a front surface side of the operation space.

* * * * *